United States Patent
Porter et al.

(10) Patent No.: US 12,161,558 B2
(45) Date of Patent: Dec. 10, 2024

(54) ARTIFICIAL VERTEBRAL ENDPLATES AND ASSOCIATED METHODS

(71) Applicant: Brigham Young University (BYU), Provo, UT (US)

(72) Inventors: Danni Joell Porter, Alpine, UT (US); Anton Bowden, Lindon, UT (US); Brian Jensen, Orem, UT (US)

(73) Assignee: Brigham Young University, Provo, UT (US)

( * ) Notice: Subject to any disclaimer, the term of this patent is extended or adjusted under 35 U.S.C. 154(b) by 30 days.

(21) Appl. No.: 17/646,394

(22) Filed: Dec. 29, 2021

(65) Prior Publication Data

US 2022/0202584 A1 Jun. 30, 2022

Related U.S. Application Data

(60) Provisional application No. 63/131,712, filed on Dec. 29, 2020.

(51) Int. Cl.
*A61F 2/44* (2006.01)
*A61F 2/30* (2006.01)

(52) U.S. Cl.
CPC ...... *A61F 2/44* (2013.01); *A61F 2002/30324* (2013.01); *A61F 2002/30784* (2013.01); *A61F 2002/3084* (2013.01); *A61F 2002/30914* (2013.01); *A61F 2002/3093* (2013.01); *A61F 2002/30963* (2013.01); *A61F 2002/30971* (2013.01); *A61F 2310/00017* (2013.01); *A61F 2310/00574* (2013.01)

(58) Field of Classification Search
CPC .............. A61F 2/44; A61F 2002/30324; A61F 2002/30784; A61F 2002/3084; A61F 2002/30914; A61F 2002/30963; A61F 2002/30971; A61F 2310/00017; A61F 2310/00574
USPC ........ 623/17.11–17.16; 606/70–71, 280–299
See application file for complete search history.

(56) References Cited

U.S. PATENT DOCUMENTS

| | | |
|---|---|---|
| 10,537,666 B2 | 1/2020 | Paddock et al. |
| 2003/0074076 A1* | 4/2003 | Ferree .............. A61F 2/28 623/17.16 |
| 2004/0068320 A1* | 4/2004 | Robie ............... A61F 2/4425 623/23.6 |
| 2004/0260286 A1* | 12/2004 | Ferree ............. A61F 2/4455 606/247 |

(Continued)

FOREIGN PATENT DOCUMENTS

| | | | |
|---|---|---|---|
| JP | 2016214866 A | 12/2016 | |
| WO | WO-2008014258 A2 * | 1/2008 | ........... A61B 17/144 |
| WO | WO-2016069811 A2 * | 5/2016 | ............. A01N 25/34 |

OTHER PUBLICATIONS

International Search Report and Written Opinion for PCT Application No. PCT/US2021/073158, mailed on May 3, 2022, 12 pages.

*Primary Examiner* — Jessica Weiss
(74) *Attorney, Agent, or Firm* — Brake Hughes Bellermann LLP

(57) ABSTRACT

In a general aspect, an apparatus can include a plate configured for implantation in a body of a patient. The plate can include a plurality of pores and be configured for placement between a cancellous bone of a spinal vertebra and a corresponding cartilaginous endplate as a replacement for a bony endplate of the spinal vertebra.

24 Claims, 9 Drawing Sheets

(56) References Cited

U.S. PATENT DOCUMENTS

| | | | |
|---|---|---|---|
| 2005/0203627 A1* | 9/2005 | Choksey | A61F 2/44 |
| | | | 623/17.14 |
| 2006/0282166 A1* | 12/2006 | Molz | A61F 2/442 |
| | | | 623/17.13 |
| 2007/0191957 A1* | 8/2007 | Anderson | A61B 17/0401 |
| | | | 623/23.52 |
| 2007/0198090 A1* | 8/2007 | Abdou | B82Y 5/00 |
| | | | 606/255 |
| 2007/0260324 A1* | 11/2007 | Joshi | A61F 2/4465 |
| | | | 623/17.11 |
| 2008/0195213 A1* | 8/2008 | Halverson | A61F 2/4425 |
| | | | 623/17.15 |
| 2012/0282302 A1 | 11/2012 | McCanless et al. | |
| 2013/0218288 A1 | 8/2013 | Fonte et al. | |
| 2014/0052256 A1* | 2/2014 | Ankney | A61B 17/1671 |
| | | | 623/17.16 |
| 2015/0289911 A1* | 10/2015 | Beyar | A61L 31/082 |
| | | | 264/154 |
| 2016/0183990 A1* | 6/2016 | Koizumi | C12M 25/02 |
| | | | 606/285 |
| 2019/0269521 A1 | 9/2019 | Shoshtaev | |

* cited by examiner

ARTIFICIAL VERTEBRAL ENDPLATES AND ASSOCIATED METHODS

CROSS-REFERENCE TO RELATED APPLICATIONS

This application is a non-provisional of, and claims priority to, U.S. Provisional Patent Application No. 63/131,712, filed on Dec. 29, 2020, entitled "Artificial Vertebral Endplate", which is incorporated by reference herein in its entirety.

TECHNICAL FIELD

This description relates to artificial vertebral endplates, fabrication of such artificial endplates and method of using such artificial endplates.

BACKGROUND

Back pain affects a significant percentage of the adult population and, based on recent trends, appears to be increasing in occurrence. In fact, back and/or spine related disorders are primary cause of adult disability. Current treatments for chronic backpain are limited and often involve spinal fusion. Although spinal fusion can be helpful in some cases, it has one of the lowest patient satisfaction ratings of common orthopedic surgeries. These low satisfaction ratings are likely due to such procedures being painful and having a long recovery time. Further, spinal fusion reduces a patient's range of motion and often requires follow up surgeries, as the decrease in mobility of fused segments puts adjacent segments under more stress, which can result in further injury to the spine.

SUMMARY

In a general aspect, an apparatus can include a plate configured for implantation in a body of a patient. The plate can include a plurality of pores and be configured for placement between a cancellous bone of a spinal vertebra and a corresponding cartilaginous endplate as a replacement for a bony endplate of the spinal vertebra.

In some implementations, the plate can be configured for osseointegration with the cancellous bone. In some implementations, the plate can be configured to facilitate fibroblast attachment.

In some implementations, the plate can have a porosity of between 30 percent and 70 percent. In some implementations, a pore of the plurality of pores can have diameter between 400 micrometers (μm) and 600 μm.

In some implementations, the plate includes a patterned plurality of carbon nanotubes. In some implementations, the plurality of carbon nanotubes can be infiltrated with carbon. In some implementations, the plate can include a stainless steel mesh coated with carbon infiltrated carbon nanotubes.

In some implementations, the plate can have a thickness between 450 micrometers (μm) and 550 μm. In some implementations, a geometric center of the plate can have a thickness that is less than a thickness of the plate at an edge of the plate. In some implementations, the plate can have a mechanical stiffness between 100 mega-pascals and 18 giga-pascals. In some implementations, the plate can include a patterned plurality of carbon nanotubes that are infiltrated with carbon, and the material stiffness of the plate can be based, in part, on an amount of carbon infiltration of the plurality of carbon nanotubes.

In some implementations, the plate can include at least one layer of biocompatible mesh coated with a biocompatible polymer.

In another general aspect, a method can include providing a substrate, and forming a patterned catalyst layer on the substrate. The patterned catalyst layer can define a template for carbon nanotube growth. The template can define a pattern for formation of a plate configured for implantation in a body of a patient. The plate can including a plurality of pores and can be configured for placement between a cancellous bone of a spinal vertebra and a corresponding cartilaginous endplate, as a replacement for a bony endplate of the spinal vertebra. The method can further include growing carbon nanotubes on the patterned catalyst layer to form the plate.

In some implementations, the method can further include infiltrating the carbon nanotubes with carbon to achieve a mechanical stiffness of the plate between 100 mega-pascals and an 18 giga-pascals.

In some implementations, the method can further include removing the plate from the substrate. In some implementations, removing the plate from the substrate can include at least one of chemical etching an interface between the plate and the substrate, or applying a mechanical force to separate the plate from the substrate.

In another general aspect, a surgical method can include forming an incision in a body of a patient, where the incision provides access to an intervertebral structure of the patient. The method can further include separating a cartilaginous endplate from a bony endplate of a vertebra of the intervertebral structure. The method can also include removing the bony endplate to expose vascularity of a cancellous bone of the vertebra. The method can still further includes placing a porous plate as a replacement for the removed bony endplate, such that a first surface of the porous plate is in contact with the exposed cancellous bone. The method can also further include positioning the cartilaginous endplate in contact with a second surface of the porous plate, the second surface of the porous plate being opposite the first surface.

In some implementations, the surgical method can include removing the cartilaginous endplate, and replacing the removed cartilaginous endplate with a tissue-engineered cartilaginous endplate.

In some implementations, the porous plate can include a patterned plurality of carbon nanotubes, where the plurality of carbon nanotubes are infiltrated with carbon. In some implementations, the plate can have a porosity between 30 percent and 70 percent. In some implementations, the porous plate can have a thickness between 450 micrometers (μm) and 550 μm. In some implementations, the porous plate can have a mechanical stiffness between 100 mega-pascals and 18 giga-pascals.

Figure 1:
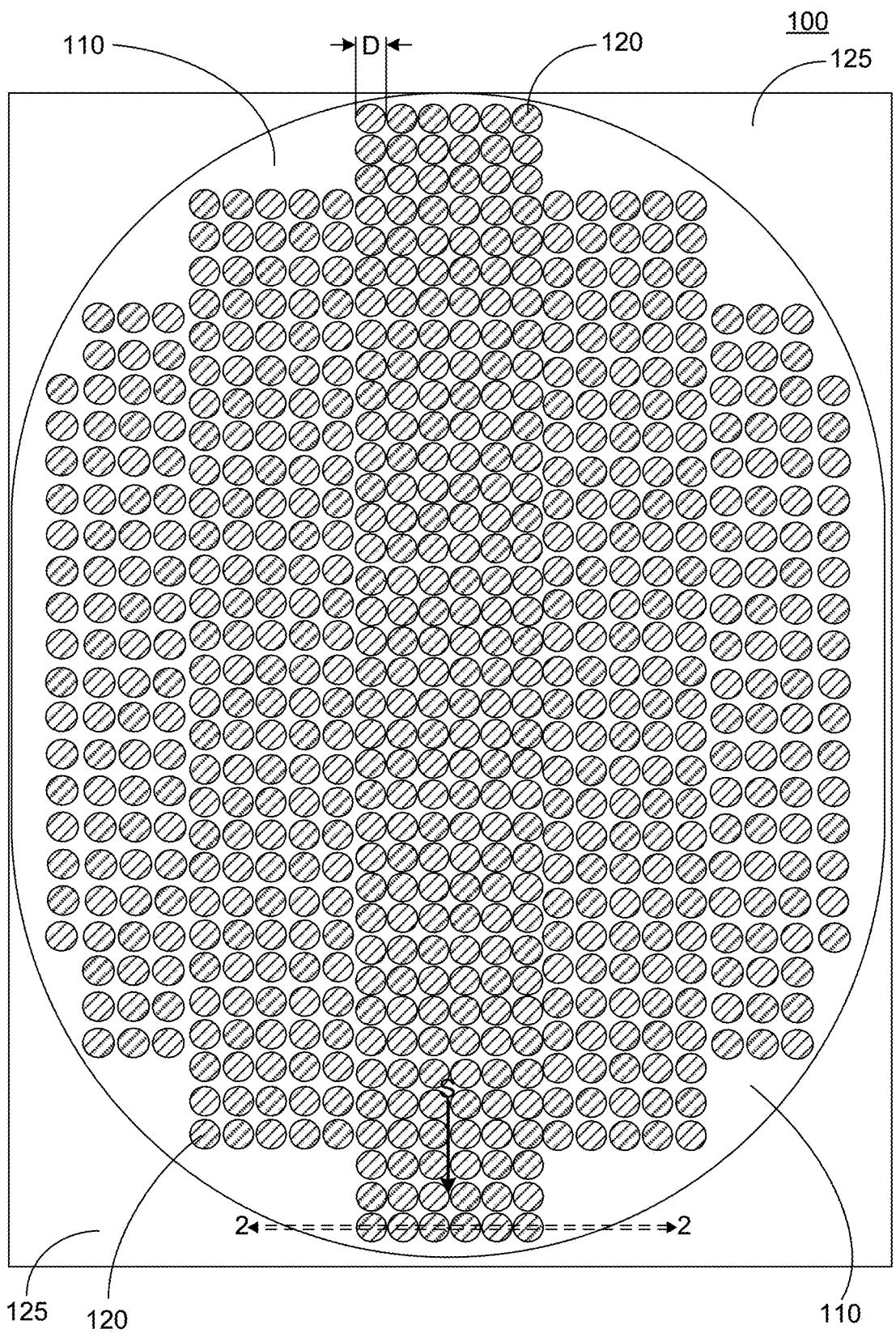
FIG. 1 is a diagram that illustrates an example template of an artificial vertebral endplate, according to an implementation.

In the drawings, which are not necessarily drawn to scale, like reference symbols may indicate like and/or similar components (elements, structures, etc.) in different views. The drawings illustrate generally, by way of example, but not by way of limitation, various implementations discussed in the present disclosure. Reference symbols shown in one drawing may or may not be repeated for the same, and/or similar elements in related views. Further, reference symbols that are repeated in multiple drawings may not be specifically discussed with respect to each of those drawings, but are provided for context between related views. Also, not all like elements in the drawings may be specifically referenced with a reference symbol when multiple instances or portions of an element are illustrated.

DETAILED DESCRIPTION

Efforts to improve treatments for spinal disorders and associated back and spine pain have focused on treatment of intervertebral discs. For instance, work has been done to identify alternative approaches such as tissue engineering, stem-cell therapies, genetic therapies, etc., for treatment of intervertebral discs. Current approaches, however, do not address repair or replacement of intervertebral endplates, which bound intervertebral discs and facilitate fluid, nutrient and waste transport between intervertebral discs and vascularity within associated spinal vertebra. Such endplates (e.g., bony endplates and cartilaginous endplates) generally degenerate simultaneously with an associated intervertebral disc (disc), where such degeneration can be progressive and result in loss of disc height (due to fluid loss), changes in nutrient, fluid and waste transport (hydraulic permeability), and/or calcification (occlusion) of the endplates. Accordingly, failure to address the contribution of endplate degeneration to resulting spinal disorders can impede the efficacy of biological approaches used to treat disc-related spine pain.

The present disclosure is directed to artificial intervertebral endplate apparatus (artificial endplates, plates, etc.), as well as methods for producing and using such artificial endplates. For instance, the present disclosure is directed to approaches for repair and/or replacement of a bony endplate (which can also be referred to as a subchondral plate) of a spinal vertebra with a porous biocompatible, osseointegrative plate that closely matches structural and mechanical properties of a healthy (natural) endplate. That is, artificial endplates described herein can mimic the hydraulic permeability (e.g., porosity) and structural characteristics (e.g., mechanical stiffness) of a healthy endplate and can, therefore, facilitate providing nutrition to, as well as providing mechanical containment and support of heavily loaded soft tissue of intervertebral discs, whether natural discs or tissue engineered discs.

As described herein, disclosed approaches for artificial endplates can have osseointegrative properties, and may also promote chondrocyte (fibroblast or cartilage) integration. In disclosed approaches, carbon-infiltrated carbon nanotube (CI-CNT) material and/or other biocompatible materials can be used to produce such an artificial endplate. Again, artificial endplates described herein, such as endplates including CI-CNT materials, can mimic the function of natural vertebral bony endplates by providing similar porosity, stiffness, mechanical strength, and hydraulic permeability, as well as osseointegration and tissue integration. Accordingly, disclosed artificial endplate implementations are bio-compatible and, e.g., for endplate implementations including CI-CNT materials, can also desirably have anti-bacterial properties.

FIG. 1 is a diagram that illustrates an example template 100 than can be used to produce an artificial vertebral endplate for replacement of a bony endplate, such as described herein. The template 100, which is shown for purposes of illustration, shows an example arrangement of an artificial endplate that can be used, at least in part, for treatment of degenerative spinal disorders. For instance, the template 100 could be used to form an artificial endplate from an appropriate material, such as a sheet (e.g., a forest) of CI-CNTs, or a sheet (or plate) of other biocompatible material, such as medical grade mesh coated (e.g., dipped, sprayed, etc.) with a biocompatible polymer, a biocompatible plate. For instance, in some implementations, the template 100 can be used to define areas 125 of artificial endplate material (e.g., a starting work piece) that are to be removed, e.g., etched using a chemical etch, a laser etch, and/or removed using another appropriate approach to define the outer edges of the artificial endplate. Further, in this example, the template 100 can be used to define a pattern of pores 120 of an artificial endplate that can also be formed along with removal of material in the areas 125.

After removal of material in the areas 125, and removal of material to define the pores 120, artificial endplate material (e.g., from the starting work piece) will remain in areas 110 in FIG. 1, as the structural portions of a resulting artificial endplate (e.g., forming the edges of the endplate, as well as defining the pores 120 of the endplate). As shown in FIG. 1, the pores 120 can have a diameter D, which, depending on the particular implementation, can be in a range of 400 micrometers (μm) and 6000 μm.

In another example implementation, the template 100 can be used as a photolithography mask to pattern a catalyst layer for producing an artificial endplate with CI-CNTs (e.g., growing a templated forest of CNTs that are then carbon infiltrated), such as in accordance with the manufacturing process illustrated in FIGS. 2A-2F, and described in further detail hereinbelow. The double-dashed line 2-2 in FIG. 1 identifies a slice of the template 100 that corresponds with side cross-sectional views of the artificial endplate shown in FIGS. 2A-2F, which are viewed along a directional line S in FIG. 1. The slice of the template 100 identified by the double-dashed line 2-2 is used, by way to example, to clearly illustrate formation of the edges and pores of an artificial endplate, without those details being obscured by structure of the associated artificial endplate that is present further along the directional line S (e.g., structure that is disposed behind the pores 120 along the direction of the line S).

Using the approaches described herein, a template, such as the template 100, or a template having a different arrangement, can be used to produce an artificial endplate (a plate) that is configured to be implanted in a body of a patient. For instance, as described herein, such artificial endplates can include a plurality of pores with respective diameters between 400 μm and 600 μm. Though, in other implementations, pores of other diameters are possible. In some implementations, such artificial endplates can have an overall porosity between 30 percent and 70% (e.g., defined by an associated template or pattern), which can depend, at least in part, on the bony endplate being replaced. In some implementations, such the example of FIG. 1, the porosity of an artificial endplate can vary across the endplate, with outer portions of the endplate having a different porosity (e.g., lower in this example) than inner portions of the endplate.

Such artificial endplates can be configured for placement between a cancellous bone of a spinal vertebra and a corresponding cartilaginous endplate as a replacement for a bony endplate of the spinal vertebra. Further, using the approaches and/or materials described herein, such artificial endplates can be osseointegrated with a corresponding spinal vertebra (e.g., a cancellous bone) and can also promote fibroblast (cartilage) attachment, such that biological attachment is achieved on both sides of the artificial endplate in an intervertebral structure of a patient.

FIGS. 2A through 2F are cross-sectional diagrams illustrating a processing flow for producing an artificial vertebral template, according to an implementation. In this example, a photolithography mask consistent with the template 100 of FIG. 1 can be used in implementing the method of FIGS. 2A-2F. As noted above, the location of the cross-sectional views of FIGS. 2A-2F in the template 100 and a resulting artificial endplate are indicated by the slice of double-dashed line 2-2 in FIG. 1.

Figure 2A:
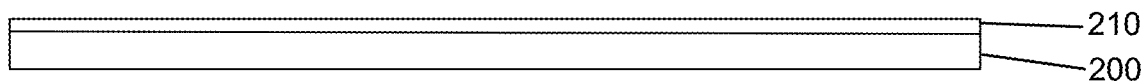
FIGS. 2A through 2F are cross-sections illustrating a processing flow for producing an artificial vertebral template, according to an implementation.

In this example, as shown in FIG. 2A, a substrate 200 can be prepared. The substrate can include, for example, a Si wafer having a buffer layer 210 disposed (formed, deposited, etc.) thereon. In this implementation, the buffer layer 210, which can be an aluminum oxide ($Al_2O_3$) layer (e.g., an approximately 40 nanometer thick alumina layer), can prevent diffusion of a catalyst for CNT growth from diffusing into the Si wafer substrate 200. In other implementations, other materials can be used for the substrate, such as metal or glass substrates.

Figure 2B:
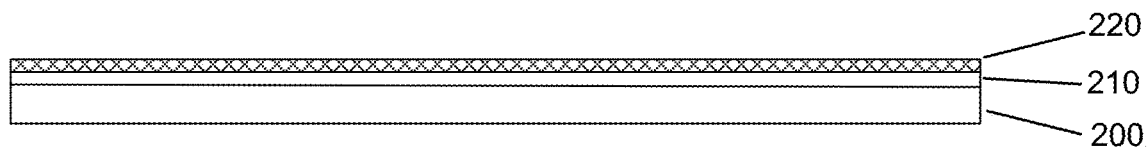
Figure 2C:
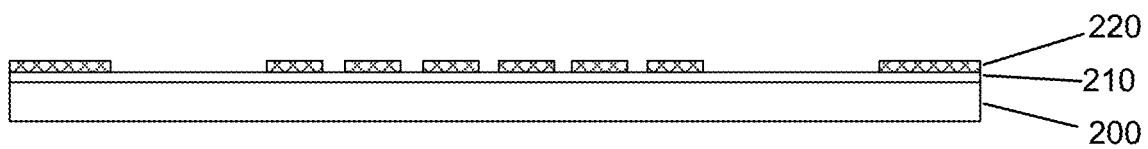

As shown in FIGS. 2B-2E, photolithography can then be performed using a photolithography mask consistent with the template 100 to form a patterned catalyst layer 230, which can be an iron (Fe) layer (e.g., a 4-7 nanometer thick Fe layer). For instance, as shown in FIG. 2B, a photoresist layer 220 can be formed on the buffer layer 210. As shown in FIG. 2C, the photoresist layer 220 can then be patterned using the photomask to define areas on the buffer layer 210 where the patterned catalyst layer 230 will be formed to define the structural portions, as well as the pores of a produced artificial endplate. Accordingly, in this example, the patterned catalyst layer 230 can have the pattern of the artificial endplate template 100 shown in FIG. 1. In other implementations, other patterns can be formed, such as patterns with different porosity, different pore sizes, different arrangement of pores, different pore shapes, etc.

Figure 2D:
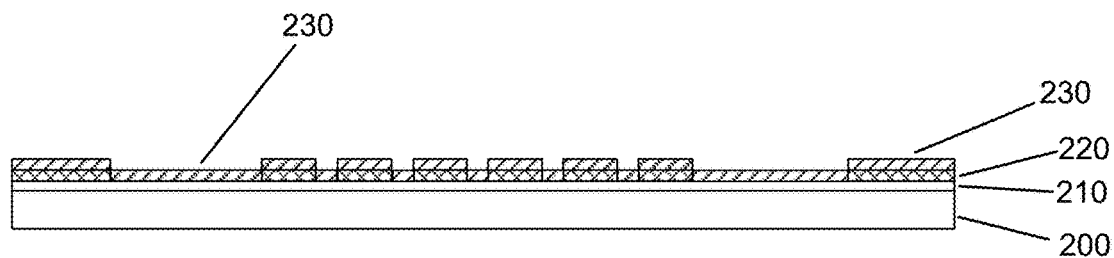
Figure 2E:
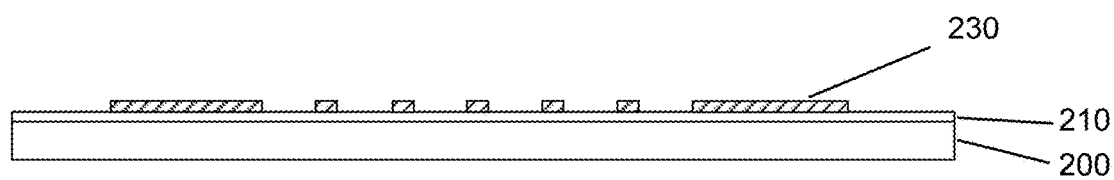

As shown in FIG. 2D a catalyst material (e.g., Fe) can be deposited and, as illustrated by FIG. 2E, a lift-off etch process can be performed to remove unwanted catalyst material and underlying photoresist 220, such that the remaining catalyst material is patterned based on the photomasking of FIG. 2C (e.g., consistent with the template 100 of FIG. 1).

Figure 2F:
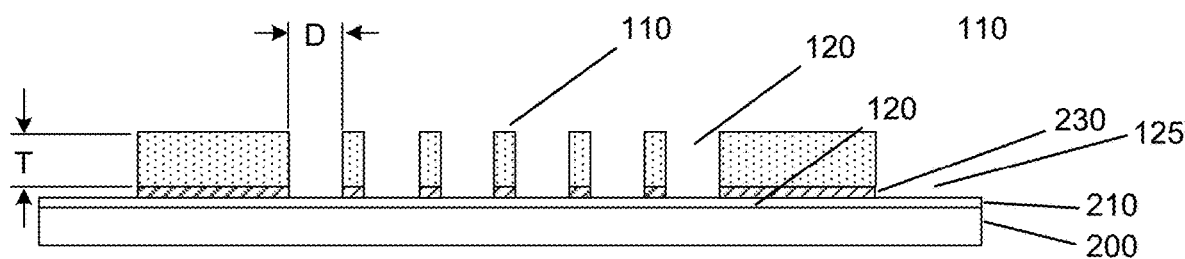

As shown in FIG. 2F, chemical vapor deposition (CVD), and subsequent carbon infiltration, can be performed to produced patterned CI-CNTs that define an artificial endplate, e.g., based on the template 100 in this example. That is, the structural area 110, as well as the pores 120 of the artificial endplate can be defined by the patterned forest of CNTs.

In some implementations, CNT growth of FIG. 2F can be performed in, for example, a tube furnace. In such approaches, the structure shown in FIG. 2E can be placed in the furnace and hydrogen gas can flow over the catalyst patterned substrate as the furnace is heated to a desired temperature (750-800 C in one implementation). This hydrogen flow can reduce any oxide that may have formed on the catalyst layer 230 (as wells as prevent formation of additional oxide). After the furnace arrives at the desired temperature, carbon nanotubes (e.g., substantially vertical carbon nanotubes) can be grown by adding a flow of ethylene gas to the hydrogen flow for a given growth time, where the growth time depends on the desired height (aspect ratio) of the CNT structures being formed. Carbon nanotube growth can then be terminated by replacing the flows of hydrogen and ethylene with an inert gas flow (e.g., an argon flow) to flush the furnace chamber and halt CNT growth. As shown in FIG. 2F, the patterned CNTs can have a height of T, which can correspond to a thickness of the resulting artificial endplate in a range of 450 μm to 550 μm. In implementations, the height (thickness) T can depend on growth time, furnace temperature, and or gas flow ratio. In some implementations, the thickness of a resulting endplate can be greater at the edges than in an center of the endplate. Such a thickness difference can result from, for example, lower catalyst thickness at the edges promoting more rapid CNT growth than in areas of higher catalyst thickness.

Further with reference to FIG. 2F, after forming (growing) CNTS on the patterned catalyst layer 230 to define the structural areas 110 and the pores 120 of an artificial endplate, carbon infiltration can be performed. Such carbon infiltration can link the CNTs together with bulk carbon to obtain a desired mechanical stiffness of the patterned CNTs (e.g., a patterned CNT forest) of the resulting artificial endplate. During carbon infiltration, the patterned CNTs of the artificial endplate can be heated to a temperature greater than the temperature used for CNT growth (e.g., in a range 850-900 C). Carbon infiltration can then be performed using different reaction gas flow rates than used for CNT growth (e.g., infiltration can be performed using a gas flow of $C_2H_2$ and $H_2$). Depending on the infiltration time and/or gas flow ratios, different mechanical stiffnesses can be achieved as result of different infiltration amounts, or percentage of infiltration. In some implementations, artificial endplates with mechanical stiffnesses ranging from 100 mega-pascals and 18 giga-pascals can be produced using the process of FIGS. 2A-2F.

After performing carbon infiltration to achieve a desired mechanical stiffness, the resulting artificial endplate can be removed from the substrate 200. It is noted that, though shown for reference in FIG. 2F, in example implementations, the patterned catalyst layer 230 can be substantially, or completely consumed during CNT growth. In some implementations, the resulting artificial endplate can be removed using a chemical etch to lift the endplate off the substrate 200. In some implementations, a mechanical force can be applied to remove (e.g., pry) the resulting artificial endplate off the substrate 200.

Figure 3:
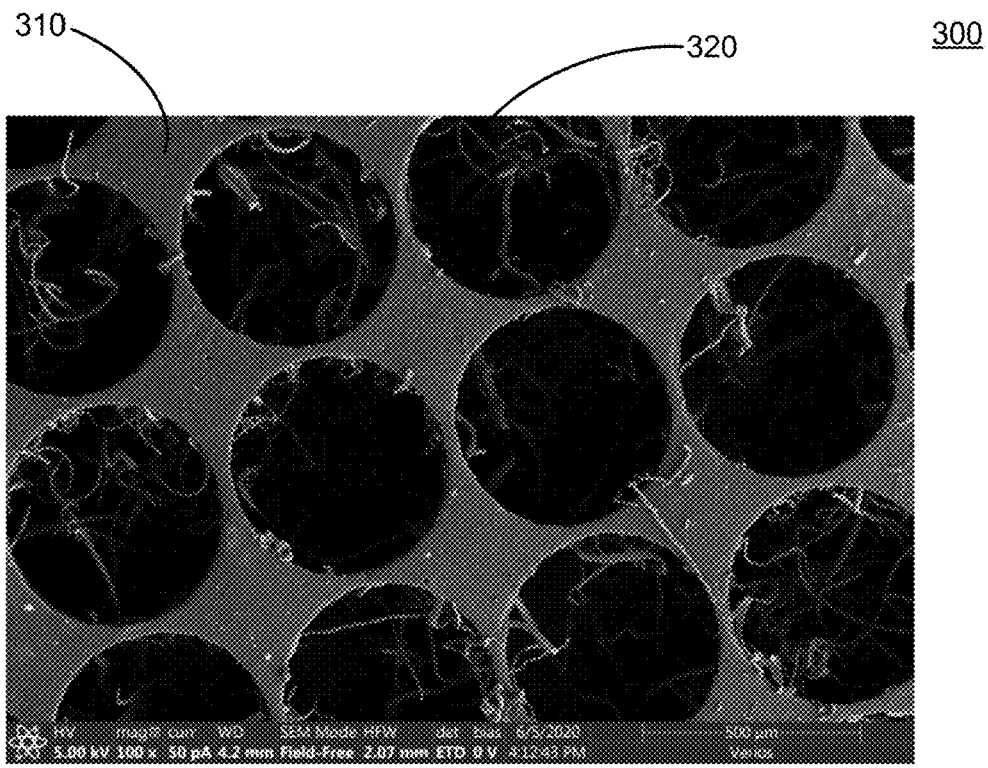
FIG. 3 is a scanning electron microscope image of a portion of an artificial vertebral endplate, according to an implementation.

FIG. 3 is a scanning electron microscope (SEM) image (a 100× image) of a portion of an artificial vertebral endplate 300, according to an implementation. In this example, the endplate 300 is a CI-CNT structure produced using the process of FIGS. 2A-2F based on the template 100 of FIG. 1. The portion of the endplate 300 shown in the SEM image of FIG. 3 includes structural portions 310 that define a plurality of pores 320 (with 500 µm diameters). The endplate 300, as shown in FIG. 3 includes stray CNTs resulting from the CNT growth process. In some implementations, the stray CNTs can be removed using a cleaning process, such a liquid rinse, oxygen plasma, or other cleaning approach.

Figure 4:
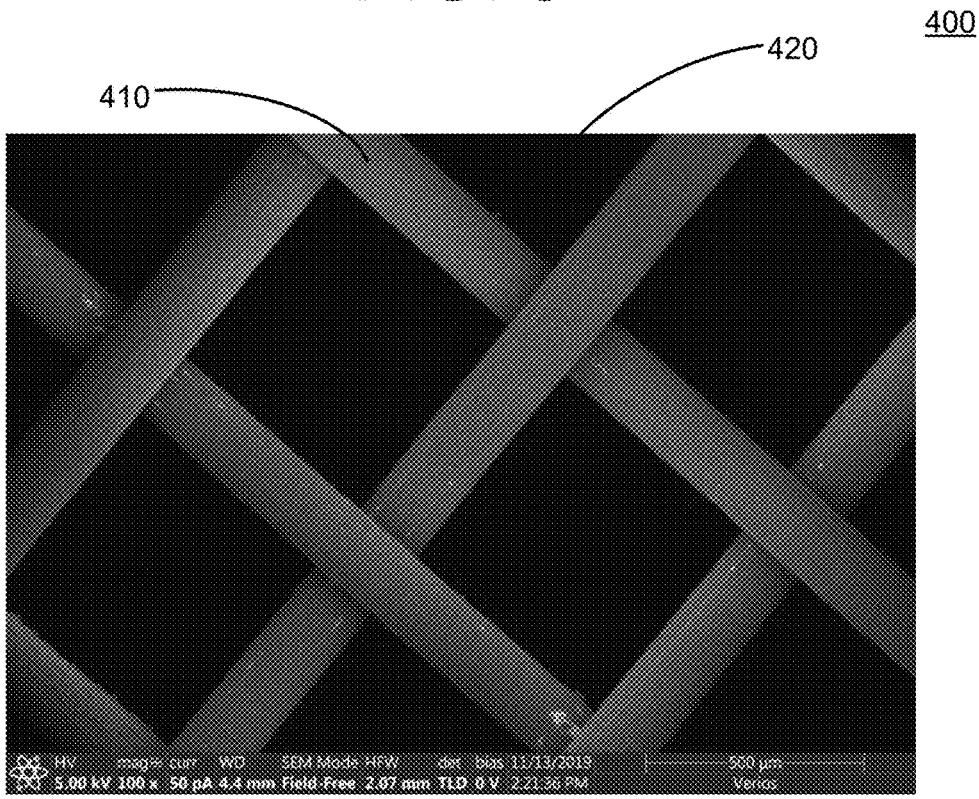
FIG. 4 is a scanning electron microscope image of a portion of an artificial vertebral endplate, according to an implementation.

FIG. 4 is a SEM image (a 100× image) of a portion of another artificial vertebral endplate 400, according to an implementation. In this example, the endplate 400 includes a CI-CNT coated stainless steel mesh, where the spacing between strands of the mesh can define a pore size of the resulting endplate 400. In this example, iron atoms present in the stainless steel mesh provide the catalyst for CNT growth. As shown in FIG. 4. The CI-CNT coated strands 410 act as the structural portions of a resulting artificial endplate 400, as well as define the associated pores 420. Such implementations, due to the use of CI-CNT coated stainless steel, are biocompatible, osseointegrative, have anti-bacterial properties and can be produced to have a range of mechanical stiffnesses comparable to natural bony endplates. In other implementations, other mesh materials and coating materials can be used to produced the endplate 400, such as described herein.

Figure 5:
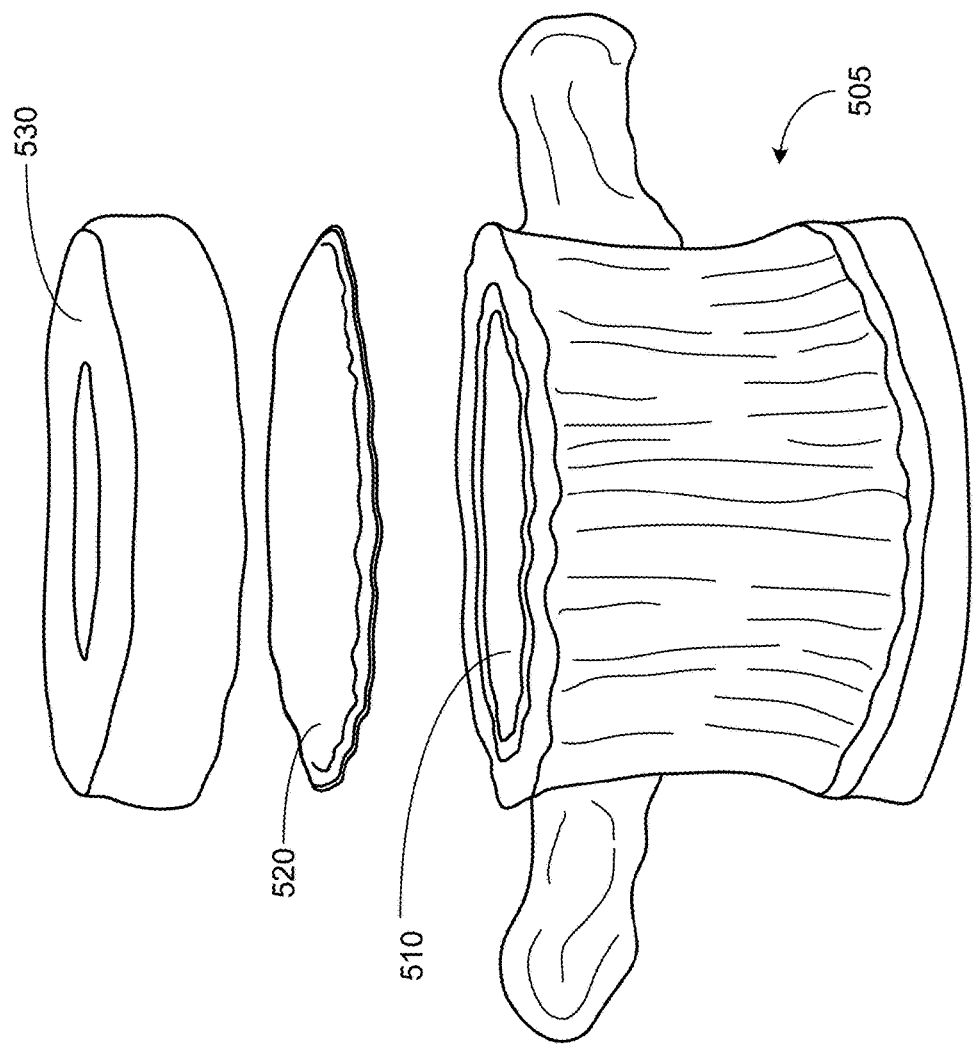
FIG. 5 is a diagram illustrating an exploded view of a vertebral structure.

FIG. 5 is a diagram illustrating an exploded view of a healthy vertebral structure 500, in which the artificial bony endplates described herein can be implemented as a therapeutic replacement for a degenerated and/or damaged natural bony endplate (e.g., spinal vertebra subchondral plate), such as in combination with other therapeutic measures to address associated degeneration of the cartilaginous endplate 520 and the intervertebral disc 530.

As shown in FIG. 5, the vertebral structure 500 (e.g., a natural and healthy vertebral structure) includes a spinal vertebra 505, a cartilaginous endplate 520 and an intervertebral disc 530. As also shown in FIG. 5, the spinal vertebra 505 includes a bony endplate 510, which can also be referred to as a subchondral plate of the spinal vertebra 505. In the vertebral structure 500, a vertebral endplate can be considered to be a bilayer that includes the cartilaginous endplate 520 and the spinal vertebra 505, which separates the intervertebral disc 530 from the spinal vertebra 505. In a healthy spinal structure, such bilayer vertebral endplates serve as a structural and operative transition (nutrition, fluid and waste pathway) between vascularized bone (a cancellous bone) in a body of the spinal vertebra 505 and the cartilaginous matrix of the intervertebral disc 530. The cartilaginous endplate 520 is a thin layer of collagen fibers (e.g., less than 0.1 millimeter thick when healthy) that transitions in mineralization levels from highly mineralized where attached to the spinal vertebra 505 to very low, or zero mineralization where attached to the intervertebral disc 530. Changes (degeneration) of the bony endplate 510 and/or the cartilaginous endplate 520 can result in intervertebral disc 530 degeneration.

The bony endplate 510 is a layer of bone that protects the cancellous bone (a vascularized bone) in the interior of the spinal vertebra 505 from high loading pressures often present in the intervertebral disc 530 that would otherwise cause damage to the disc. While different mechanisms can lead to degeneration of the various elements of the vertebral structure 500, the health of each element is dependent on the health of the other elements. Accordingly, addressing degeneration of the cartilaginous endplate 520 and/or the intervertebral disc 530, without addressing associated degeneration of the bony endplate 510 (e.g., whether causative of, or resultant from degeneration of the other elements) may be therapeutically ineffective at resolving spinal disorders and associated back and spine pain. Examples of degenerative conditions that can result in spinal disorders include impairment of nutritional pathways in the bony endplate 510 and/or the cartilaginous endplate 520. For instance, mechanical loading can be a determinant of bony endplate thickness and porosity, which can result in nutritional pathway impairment.

Figure 7:
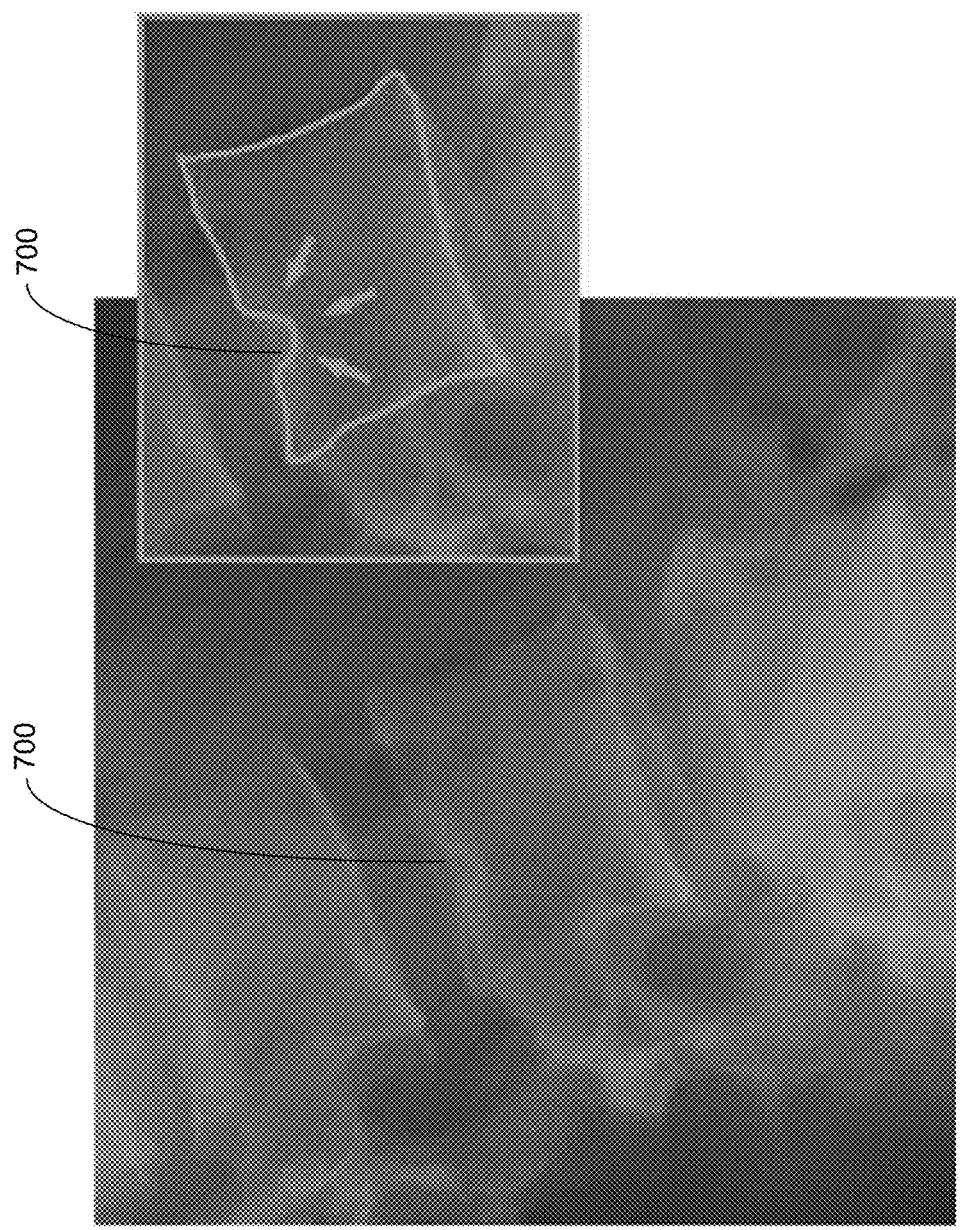
FIG. 7 are x-ray photos illustrating a Schmorl's node defect in a spinal vertebral.

Endplate penetration, e.g., penetration of the nucleus pulposus of the intervertebral disc 530 into the vascularized cancellous bone (a so called Schmorl's node as shown in FIG. 7), can result in both structural and biochemical changes to the intervertebral disc 530 that can cause degeneration of the intervertebral disc 530. That is, degeneration of the intervertebral disc 530 can be caused by structural damage to the bony endplate 510, where this type of structural damage can more easily occur easily with advancing age, as bone mass is lost, thus reducing bony endplate strength.

Figure 6B:
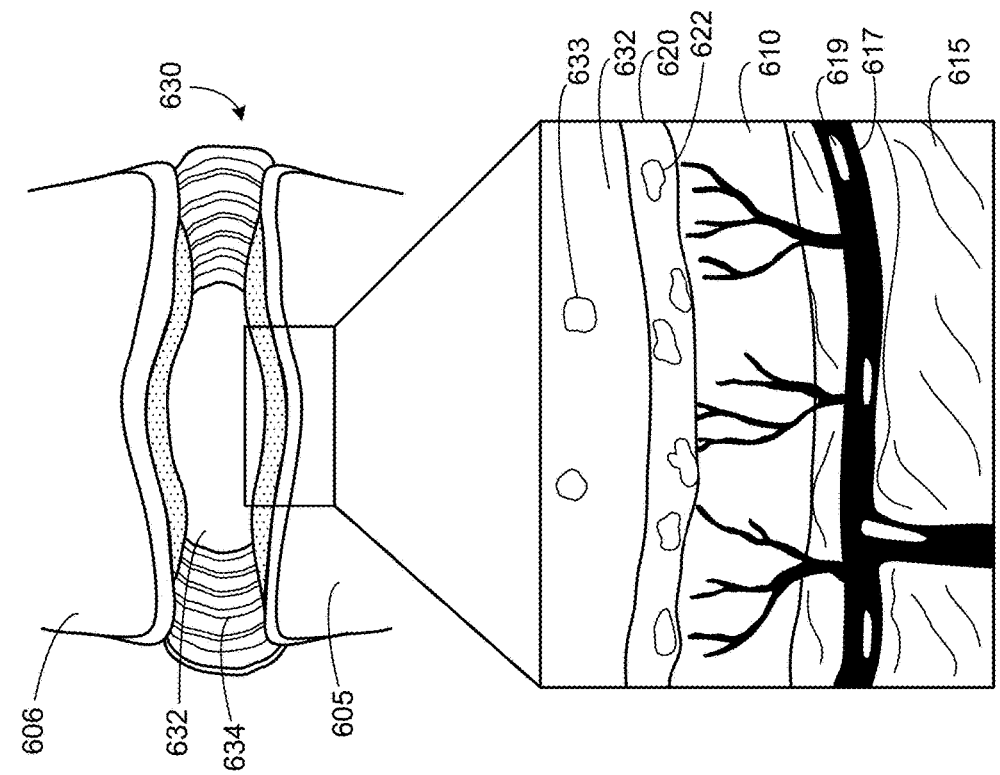
FIG. 6B is a diagram illustrating a degenerated intervertebral structure.
Figure 6A:
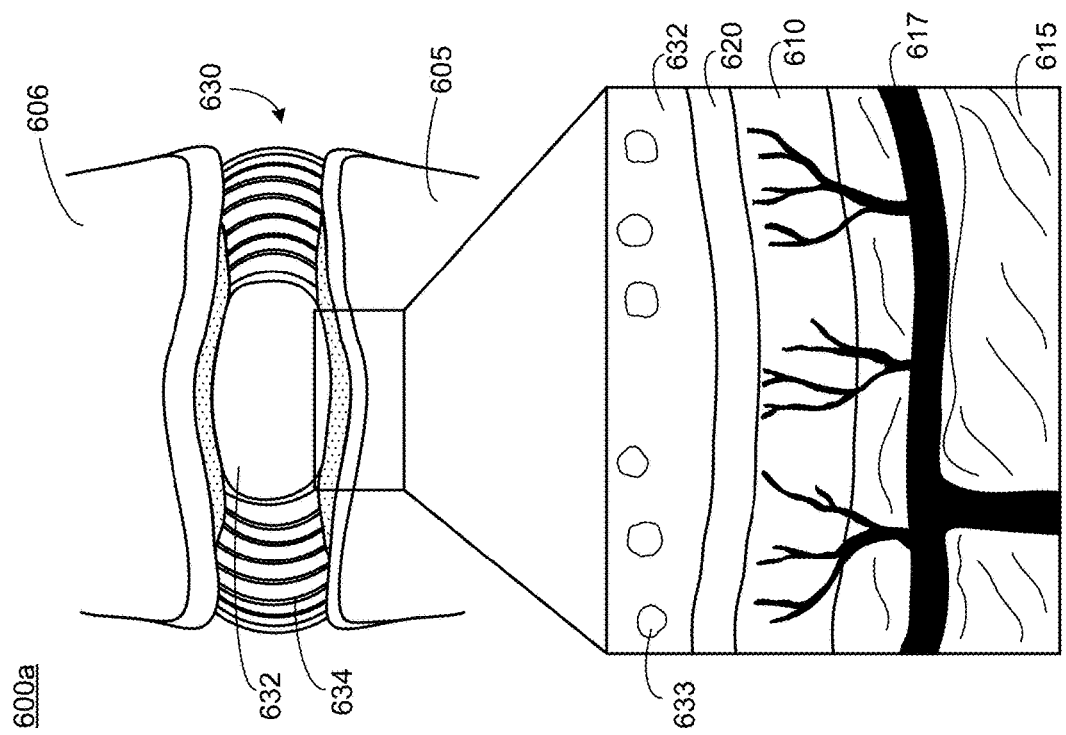
FIG. 6A is a diagram illustrating a healthy intervertebral structure.

FIG. 6A is a diagram illustrating a cross-sectional view of a healthy intervertebral structure 600a, while FIG. 6B is a diagram illustrating a cross-section view of a degenerated intervertebral structure 600b (the healthy intervertebral structure 600a after degeneration). In each of FIGS. 6A and 6B, the lower portion of the diagram illustrates a magnified view of a corresponding inset shown in respective upper portions of the FIGS. 6A and 6B.

The healthy intervertebral structure 600a and the degenerated intervertebral structure 600b, as shown in FIGS. 6A and 6B include a vertebra 605, a vertebra 606 and a intervertebral disc 630. The intervertebral disc 630 includes an nucleus pulposus 632 and an annulus fibrosus 634 that surrounds the nucleus pulposus 632. Nutrition of the intervertebral disk 630 depends on diffusion across the vertebral endplate (e.g., a bilayer including a bony endplate 610 and a cartilaginous endplate 620). As shown in FIG. 6A, in this example, the bony endplate 610 provides strength to keep the intervertebral disk 630 from bulging into a cancellous bone 615 (e.g., vascularized bond) of the vertebra 605. That is, the bony endplate 610 is a thin layer of porous bone that provides structural support for the healthy intervertebral structure healthy intervertebral structure 600a, while still allowing nutrients from the vascularized vertebral body (e.g., cancellous bone 615) to the intervertebral disc 630.

As can be seen from a comparison of FIGS. 6A and 6B, morphology of the bony endplate 610 is an important balance between strength to keep the intervertebral disc 630 from bulging into the cancellous bone 615 of the vertebra 605 and allowing enough nutrients through from the vascularized cancellous bone 615 to the non-vascularized intervertebral disc 630. This nutrient transfer is very important because the intervertebral disc 630 depends on it for all nutrition.

However, as shown in FIG. 6B, if too much fluid can pass through the bony endplate 610 (e.g., due to degeneration of the bony endplate 610), the intervertebral disc 630 can become compressed (as shown in FIG. 6B) and will cause the healthy intervertebral structure 600a to degenerate. For instance (as shown by a comparison of FIGS. 6A and 6B), degeneration of the healthy intervertebral structure 600a can cause an amount of nutrients 633 in the nucleus pulposus 632 to be reduced, calcification 622 of the bony endplate 610 and the cartilaginous endplate 620, and occlusion of vascularity 617 in the cancellous bone. Once degeneration of the healthy intervertebral structure 600a begins, it can be progress and accelerate as the degeneration becomes more pronounced.

Intevertebral disc degeneration has been linked to changing morphology in associated vertebral endplates (e.g, endplates responsible for providing a pathway to and from the intervertebral disc. Accordingly, replacing degenerated endplates is an important part of being able to effectively replace an intervertabral disc. As discussed herein, the described artificial endplates can be produced to match the morphology of a healthy bony endplate. Accordingly, use of such artificial endplates to replace degenerated vertebral endplates is therapeutically advantageous for surgical repair of intervertrable structures.

FIG. 7 is x-ray photos that illustrate a Schmorl's node defect 700 in a spinal vertebra. As discuss above, the Schmorl's node defect 700 is the result of a fracture in the bony endplate of a spinal vertebra, e.g., due to degeneration of and/or overstress of the bony endplate, that results in the nucleus pulposus of the adjacent intervertebral disc to penetrate the cancellous bone of the fractured vertebra. This can occlude the vascularity of the cancellous bone and lead to further degeneration of the affected intervertebral structure. Use of the artificial endplates described herein to replace such fractured bony endplates can prevent further degeneration, and/or repair degeneration of an intervertebral structure due to such Schmorl's node defects.

Figure 8:
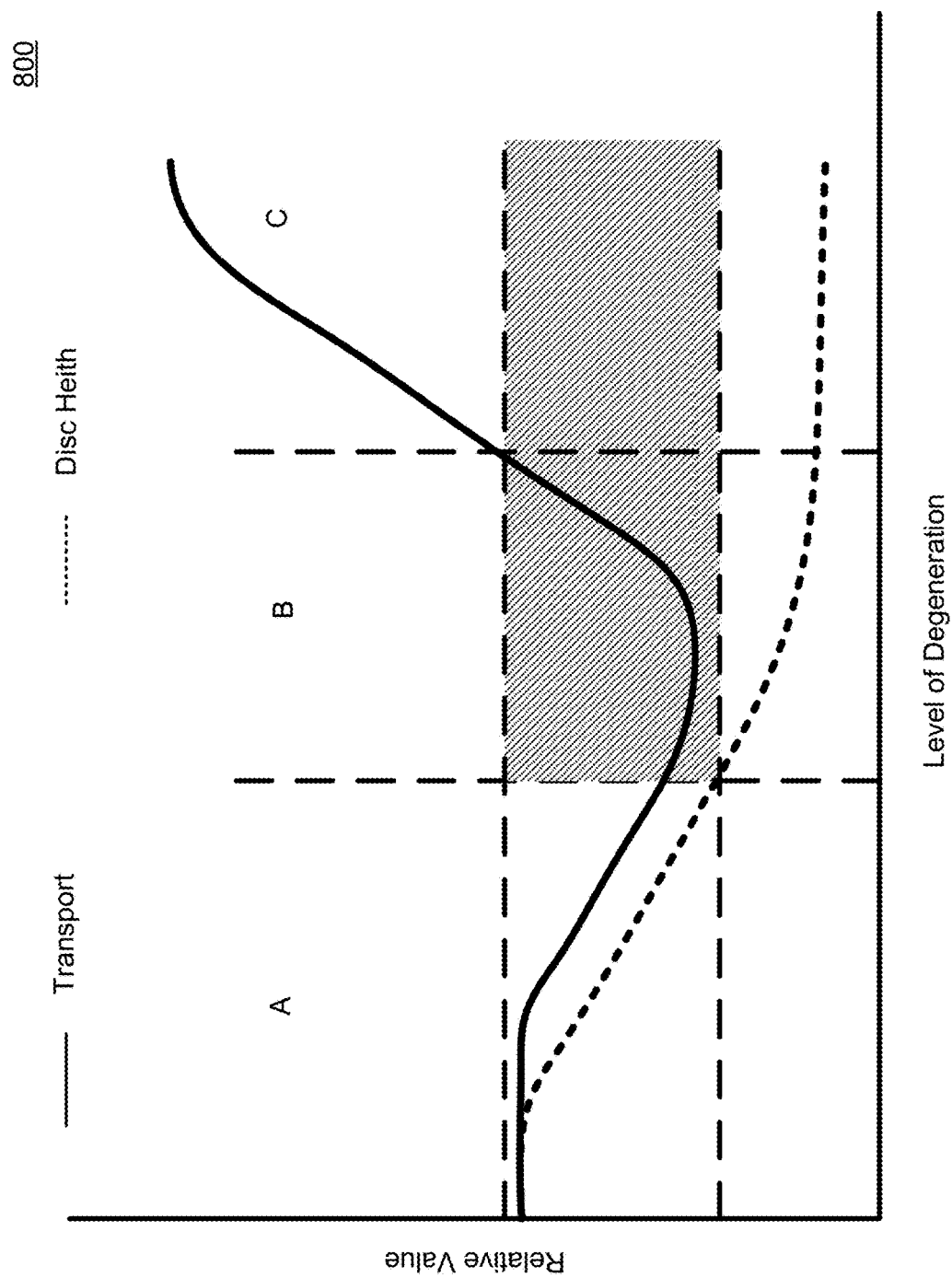
FIG. 8 is graph illustrating intervertebral disc transport properties and height as a function of disc degeneration.

FIG. 8 is graph 800 illustrating intervertebral disc transport properties and intervertebral disc height as a function of disc degeneration. The graph 800 includes three regions A, B and C, where region A corresponds with a healthy intervertebral structure, region B corresponds with early degeneration and region C corresponds with advanced degeneration.

Referring to region A of the graphs 800, it can be seen that there is a range of transport (fluid, nutrition and waste transport) in the intervertebral structure that provides for a healthy balance between transport and disc height. As shown by region B of the graph 800, as the intervertebral structure begins to degenerate, transport can be impeded, such as by changes in morphology of the vertebral endplate, and disc height can be reduced. As shown by region C of the graph, as degeneration advances, transport increases, but disc height remains decreased due to the increased transport causing fluid loss from the intervertebral disc. The relationships shown in the graph 800 further demonstrate that efficacy of surgical intervention to address intervertebral generation can be improved using the artificial endplates and associated approaches described herein.

Figure 9:
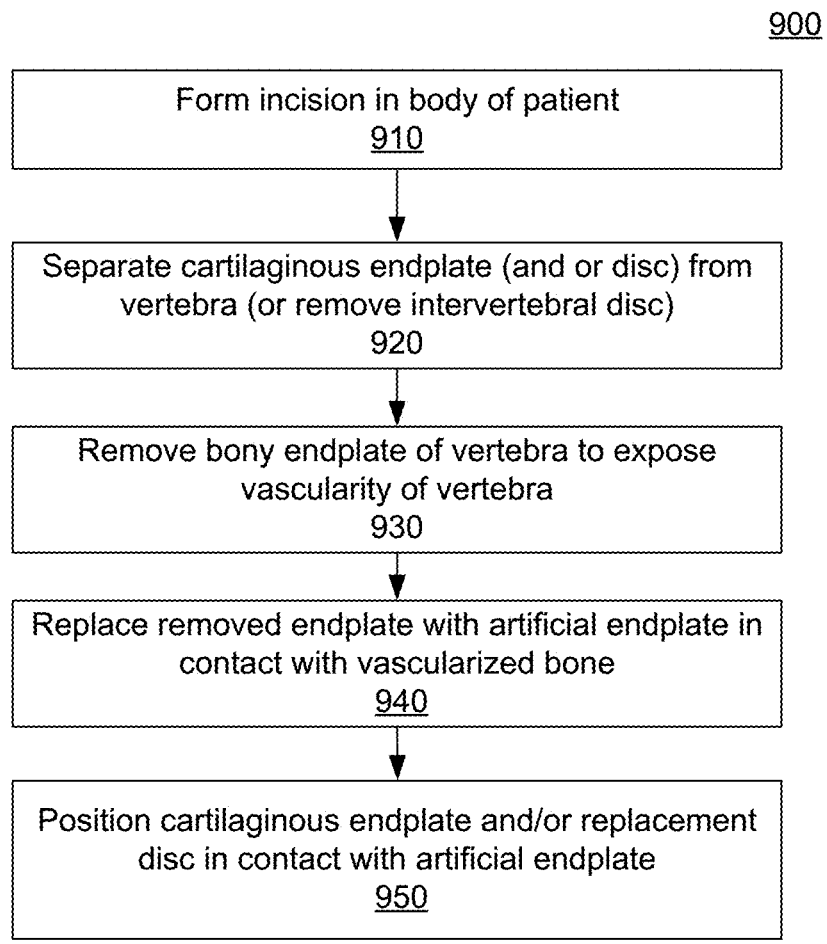
FIG. 9 is a flowchart illustrating a surgical method for replacement of a degraded vertebral endplate with an artificial vertebral endplate, according to an implementation.

FIG. 9 is a flowchart illustrating a surgical method 900 for replacement of a degraded vertebral endplate with an artificial vertebral endplate, according to an implementation. The method 900, at operation 910, includes forming an incision in a body of a patient. The incision, which can be anterior, lateral or posterior depending on the location of the affected vertebra in the patient's spine, can provide access to an associated intervertebral structure of the patient.

At operation 920, the method 900 includes separating a cartilaginous endplate (and an associated intervertebral disc) from a bony endplate of a vertebra of the intervertebral structure. At operation 930, the method 900 includes removing the bony endplate to expose vascularity of a cancellous bone of the vertebra. The bony endplate can be removed using orthopedic surgical tools, such as a saw and/or or a compressive (e.g., pounded in) tool.

At operation 940, the method 900 can include placing a porous plate as a replacement for the removed bony endplate. In some implementations, the porous plate can include multiple portions or pieces, such as for vertebra assessed laterally. At operation 940, the porous plate can be an artificial endplate, such as those described herein, and can be placed such that a first surface of the porous plate is in contact with the exposed vascularity of the cancellous bone. At operation 950, the method 900 can include positioning the cartilaginous endplate, e.g., including the intervertebral disc or a replacement intervertebral disc structure, in contact with a second surface of the porous plate, where the second surface of the porous plate is opposite the first surface.

In some implementations, the operation 930 of the method 900 can include removing the cartilaginous endplate (including an associated intervertebral disc) and replacing, at operation 950, the removed cartilaginous endplate (and associated intervertebral disc) with a tissue-engineered cartilaginous endplate and disc, such as an engineered collagen matrix.

As noted above, replacement of a vertebral endplate, e.g., using the artificial endplates and associated methods described herein, can be used as part of an intervertebral disc replacement procedure, which can help prevent disc degeneration as a result of damage to the original endplate, and/or to aid in cell therapy if the existing endplate does not allow sufficient nutrients to pass from vascularity of an associated vertebra, or allows too much fluid to outflow from the intervertebral disc, resulting in dehydration of the disc and loss of disc height. Replacing damaged or degenerated vertebral endplates can make approaches for treating degenerative intervertebral discs more viable. For instance, some potential treatments, where having a replacement bony endplate that will allow the appropriate fluid flow and nutrient supply to an adjacent intervertebral disc, are disc replacement with tissue engineered discs, cellular approaches to disc repair (stem cell therapy), genetic engineering approaches, and other disc transplants approaches.

It will be understood that, in this description, when an element, such as a layer, a region, or a substrate, is referred to as being on, connected to, electrically connected to, coupled to, or electrically coupled to another element, it may be directly on, connected or coupled to the other element, or one or more intervening elements may be present. In contrast, when an element is referred to as being directly on, directly connected to or directly coupled to another element or layer, there are no intervening elements or layers present. Although the terms directly on, directly connected to, or directly coupled to may not be used throughout the detailed description, elements that are shown as being directly on, directly connected or directly coupled can be referred to as such. The claims of the application may be amended to recite exemplary relationships described in the specification or shown in the figures.

As used in this specification, a singular form may, unless definitely indicating a particular case in terms of the context, include a plural form. Spatially relative terms (e.g., over, above, upper, under, beneath, below, lower, and so forth) are intended to encompass different orientations of the device in use or operation in addition to the orientation depicted in the figures. In some implementations, the relative terms above and below can, respectively, include vertically above and vertically below. In some implementations, the term adjacent can include laterally adjacent to or horizontally adjacent to.

While certain features of the described implementations have been illustrated as described herein, many modifications, substitutions, changes and equivalents will now occur to those skilled in the art. It is, therefore, to be understood that the appended claims are intended to cover all such modifications and changes as fall within the scope of the implementations. It should be understood that they have been presented by way of example only, not limitation, and various changes in form and details may be made. Any portion of the apparatus and/or methods described herein may be combined in any combination, except mutually exclusive combinations. The implementations described herein can include various combinations and/or sub-combinations of the functions, components and/or features of the different implementations described.

What is claimed is:

1. An apparatus comprising:
a plate including a plurality of pores, the plate being configured for placement between a cancellous bone of a spinal vertebra and a corresponding cartilaginous endplate in a body of a patient as a replacement for a bony endplate of the spinal vertebra, such that a first surface of the plate is in contact with the cancellous bone and a second surface of the plate is in contact with the cartilaginous endplate, the plate being configured such that the first surface promotes osseointegration of the cancellous bone with the plate and the second surface promotes chondrocyte integration of the cartilaginous endplate with the plate,
the plate including a patterned plurality of carbon nanotubes, the patterned plurality of carbon nanotubes being infiltrated with carbon.

2. The apparatus of claim 1, wherein the plate is configured to facilitate fibroblast attachment.

3. The apparatus of claim 1, wherein the plate has a porosity of between 30 percent and 70 percent.

4. The apparatus of claim 1, wherein a pore of the plurality of pores has a diameter between 400 micrometers (μm) and 600 μm.

5. The apparatus of claim 1, wherein the plate has a thickness between 450 micrometers (μm) and 550 μm.

6. The apparatus of claim 1, wherein a geometric center of the plate has a thickness that is less than a thickness of the plate at an edge of the plate.

7. The apparatus of claim 1, wherein the plate has a mechanical stiffness between 100 mega-pascals and 18 giga-pascals.

8. The apparatus of claim 7, wherein the mechanical stiffness of the plate is based, in part, on an amount of carbon infiltration of the patterned plurality of carbon nanotubes.

9. A method comprising:
providing a substrate;
forming a patterned catalyst layer on the substrate, the patterned catalyst layer defining a template for carbon nanotube growth, the template defining a pattern for formation of:
a plate configured for implantation in a body of a patient, the plate including a plurality of pores and being configured for placement between a cancellous bone of a spinal vertebra and a corresponding cartilaginous endplate as a replacement for a bony endplate of the spinal vertebra; and
growing carbon nanotubes on the patterned catalyst layer to form the plate.

10. The method of claim 9, further comprising infiltrating the carbon nanotubes with carbon to achieve a mechanical stiffness of the plate between 100 mega-pascals and 18 giga-pascals.

11. The method of claim 9, further comprising removing the plate from the substrate.

12. The method of claim 11, wherein removing the plate from the substrate includes at least one of:
chemical etching an interface between the plate and the substrate; or
applying a mechanical force to separate the plate from the substrate.

13. A surgical method comprising:
forming an incision in a body of a patient, the incision providing access to an intervertebral structure of the patient;
separating a cartilaginous endplate from a bony endplate of a vertebra of the intervertebral structure;
removing the bony endplate to expose vascularity of a cancellous bone of the vertebra;
placing a porous plate as a replacement for the removed bony endplate, such that a first surface of the porous plate is in contact with the exposed vascularity of the cancellous bone; and
positioning the cartilaginous endplate in contact with a second surface of the porous plate, the second surface of the porous plate being opposite the first surface.

14. The surgical method of claim 13, further comprising:
removing the cartilaginous endplate; and
replacing the removed cartilaginous endplate with a tissue-engineered cartilaginous endplate.

15. The surgical method of claim 13, wherein the porous plate:
includes a patterned plurality of carbon nanotubes, the patterned plurality of carbon nanotubes being infiltrated with carbon; and
has a porosity between 30 percent and 70 percent.

16. The surgical method of claim 13, wherein the porous plate has:
a thickness between 450 micrometers (μm) and 550 μm; and
a mechanical stiffness between 100 mega-pascals and 18 giga-pascals.

17. An apparatus comprising:
a plate including a plurality of pores, the plate being configured for placement between a cancellous bone of a spinal vertebra and a corresponding cartilaginous endplate in a body of a patient as a replacement for a bony endplate of the spinal vertebra, such that a first surface of the plate is in contact with the cancellous bone and a second surface of the plate is in contact with the cartilaginous endplate, the plate being configured such that the first surface promotes osseointegration of the cancellous bone with the plate and the second surface promotes chondrocyte integration of the cartilaginous endplate with the plate,
the plate including a stainless steel mesh coated with carbon infiltrated carbon nanotubes.

18. The apparatus of claim 17, wherein the plate is configured to facilitate fibroblast attachment.

19. The apparatus of claim 17, wherein the plate has a porosity of between 30 percent and 70 percent.

20. The apparatus of claim 17, wherein a pore of the plurality of pores has a diameter between 400 micrometers (μm) and 600 μm.

21. The apparatus of claim 17, wherein the plate has a thickness between 450 micrometers (μm) and 550 μm.

22. The apparatus of claim 17, wherein a geometric center of the plate has a thickness that is less than a thickness of the plate at an edge of the plate.

23. The apparatus of claim 17, wherein the plate has a mechanical stiffness between 100 mega-pascals and 18 giga-pascals.

24. The apparatus of claim 23, wherein the mechanical stiffness of the plate is based, in part, on an amount of carbon infiltration of the carbon infiltrated carbon nanotubes.

* * * * *